United States Patent
Cohen et al.

(10) Patent No.: US 12,082,881 B2
(45) Date of Patent: Sep. 10, 2024

(54) VISUALIZING MULTIPLE PARAMETERS OVERLAID ON AN ANATOMICAL MAP

(71) Applicant: BIOSENSE WEBSTER (ISRAEL) LTD., Yokneam (IL)

(72) Inventors: Benjamin Cohen, Haifa (IL); Aharon Turgeman, Zichron Ya'acov (IL); Natan Sharon Katz, Atlit (IL); Lior Zar, Poria Illit (IL); Yair Palti, Herzelia (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 569 days.

(21) Appl. No.: 17/208,762

(22) Filed: Mar. 22, 2021

(65) Prior Publication Data

US 2022/0296301 A1    Sep. 22, 2022

(51) Int. Cl.
*A61B 34/10*    (2016.01)

(52) U.S. Cl.
CPC ........ *A61B 34/10* (2016.02); *A61B 2034/105* (2016.02)

(58) Field of Classification Search
None
See application file for complete search history.

(56) References Cited

U.S. PATENT DOCUMENTS

| | | | |
|---|---|---|---|
| 5,391,199 A | 2/1995 | Ben Haim | |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |
| 10,470,682 B2 | 11/2019 | Deno | |
| 2002/0065455 A1 | 5/2002 | Ben Haim | |
| 2003/0120150 A1 | 6/2003 | Govari | |
| 2004/0068178 A1 | 4/2004 | Govari | |
| 2012/0184863 A1 | 7/2012 | Harlev | |
| 2013/0151275 A1 | 6/2013 | Thiers | |
| 2016/0022375 A1* | 1/2016 | Blake | G16H 50/00 600/424 |
| 2016/0242667 A1* | 8/2016 | Fay | A61B 5/6859 |
| 2017/0202469 A1 | 7/2017 | Scharf | |
| 2017/0360319 A1* | 12/2017 | Hagfors | A61B 5/367 |
| 2018/0144828 A1* | 5/2018 | Baker | G16H 30/40 |
| 2019/0099098 A1 | 4/2019 | Klebanov | |

(Continued)

FOREIGN PATENT DOCUMENTS

| | | | | |
|---|---|---|---|---|
| CA | 2713305 A1 * | 2/2012 | ......... | A61B 5/04028 |
| EP | 3750478 A1 | 12/2020 | | |
| WO | WO1996005768 A1 | 2/1996 | | |

OTHER PUBLICATIONS

European Search Report for corresponding EPA No. 22163204.5 dated Jul. 28, 2022.

*Primary Examiner* — Santiago Garcia

(57) ABSTRACT

A system includes a processor and a display. The processor is configured to: (i) receive a first dataset corresponding to a first property of an organ of a patient, and a second dataset corresponding to a second property of the organ, (ii) assign a first visual attribute to the first property and a second visual attribute to the second property, and (iii) produce a map of the organ including an overlay of the first and second visual attributes. The display is configured to display the map.

6 Claims, 2 Drawing Sheets

(56) References Cited

U.S. PATENT DOCUMENTS

| | | | |
|---|---|---|---|
| 2020/0027559 A1* | 1/2020 | Baker | G16H 50/70 |
| 2020/0060567 A1* | 2/2020 | Zeidan | A61B 5/361 |
| 2020/0074664 A1* | 3/2020 | Weber | G06T 17/00 |
| 2020/0126666 A1* | 4/2020 | Baker | G16H 15/00 |
| 2020/0237452 A1* | 7/2020 | Wolf | G06F 3/048 |
| 2020/0273552 A1* | 8/2020 | Wolf | A61B 5/02042 |
| 2020/0273581 A1* | 8/2020 | Wolf | G16H 40/63 |
| 2020/0367751 A1* | 11/2020 | Vandersickel | A61B 5/316 |
| 2022/0079424 A1* | 3/2022 | Street | A61B 1/000094 |
| 2022/0362162 A1* | 11/2022 | Gao | A61K 31/688 |
| 2023/0147888 A1* | 5/2023 | Toth | A61B 5/748 |
| | | | 345/440 |
| 2023/0148421 A1* | 5/2023 | Cowperthwait | G09B 23/285 |
| | | | 434/265 |

* cited by examiner

VISUALIZING MULTIPLE PARAMETERS OVERLAID ON AN ANATOMICAL MAP

FIELD OF THE INVENTION

The present invention relates generally to medical procedures, and particularly to methods and systems for improving visualization of multiple parameters overlaid on an anatomical map.

BACKGROUND OF THE INVENTION

Various techniques for visualizing information on anatomical maps have been published.

For example, U.S. Patent Application Publication No. 2019/0099098 describes a system that includes a display device configured to present a cardiac map, and a processing unit. The processing unit is configured to: receive electrical signals, generate the cardiac map, and facilitate display of the cardiac map, where each electrical signal corresponds to a map location. The processing unit is also configured to receive a user selection of a selected portion of the cardiac map, the selected portion including a set of map locations, each of the set of map locations corresponding to an electrical signal of a set of signals that is a subset of the received electrical signals. The set of map locations has a first spatial arrangement and the processing unit is configured to facilitate display of a set of electrical signal representations, each representation corresponding to one of the set of electrical signals, the set of electrical signal representations having a second spatial arrangement, which corresponds to the first spatial arrangement.

U.S. Patent Application Publication No. 2017/0202469 describes methods of generating a graphical representation of cardiac information on a display screen. The method comprises: electronically creating or acquiring an anatomical model of the heart including multiple cardiac locations, electronically determining a data set of source information corresponding to cardiac activity at the multiple cardiac locations, and electronically rendering the data set of source information in relation to the multiple cardiac locations on the display screen.

U.S. Pat. No. 10,470,682 describes a system for determining electrophysiological data comprising an electronic control unit. The electronic control unit is configured to acquire electrophysiology signals from a plurality of electrodes of one or more catheters, select at least one clique of electrodes from the plurality of electrodes to determine a plurality of local electrical field data points, determine the location and orientation of the plurality of electrodes, process the electrophysiology signals from the at least one clique from a full set of bipole subcliques to derive the local electrical field data points associated with the at least one clique of electrodes, derive at least one orientation independent signal from the at least one clique of electrodes from the information content corresponding to weighted parts of electrogram signals, and display or output catheter orientation independent electrophysiologic information to a user or process.

U.S. Patent Application Publication No. 2013/0151275 describes systems and methods that allow a trial planner to visualize clinical capacity available in different geographic locations in the form of icons arranged according to geography. In certain aspects, the invention provides a display including icons depicting research capacity in a plurality of geographical areas. Each icon has an aspect that depicts an aggregate capacity of a plurality of research centers that are located in the geographical region. The capacity can relate to available patient population, clinical capabilities, or local environment.

SUMMARY OF THE INVENTION

An embodiment of the present invention that is described herein provides a system including a processor and a display. The processor is configured to: (i) receive a first dataset corresponding to a first property of an organ of a patient, and a second dataset corresponding to a second property of the organ, (ii) assign a first visual attribute to the first property and a second visual attribute to the second property, and (iii) produce a map of the organ including an overlay of the first and second visual attributes. The display is configured to display the map.

In some embodiments, the first dataset includes first measurements of the first property and the second dataset includes second measurements of the second property, the first visual attribute includes a color group including multiple colors, and the second visual attribute includes a texture group including multiple texture types, and the processor is configured to map the first measurements into respective colors of the color group, and the second measurements into respective textures of the texture group. In some embodiments, the map includes multiple sections on a surface of the organ, each of the multiple sections includes at least one of the first and second measurements, and the processor is configured, at each of the multiple sections, to: (a) check for the first and second measurements, and (b) assign to the map at least one of: (i) a color of the respective colors, which are corresponding to the first measurements, and (ii) a texture of the textures, which are corresponding to the second measurements. In yet other embodiments, the organ includes a heart, and the first and second properties are selected from a list of properties consisting of: a voltage, a local activation time (LAT), a cycle length (CL) of an atrial fibrillation, and a standard deviation (STD) of the CL.

There is additionally provided, in accordance with an embodiment of the present invention, a method including receiving a first dataset corresponding to a first property of an organ of a patient, and a second dataset corresponding to a second property of the organ. A first visual attribute is assigned to the first property, and a second visual attribute is assigned to the second property. A map of the organ including an overlay of the first and second visual attributes, is produced and displayed.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
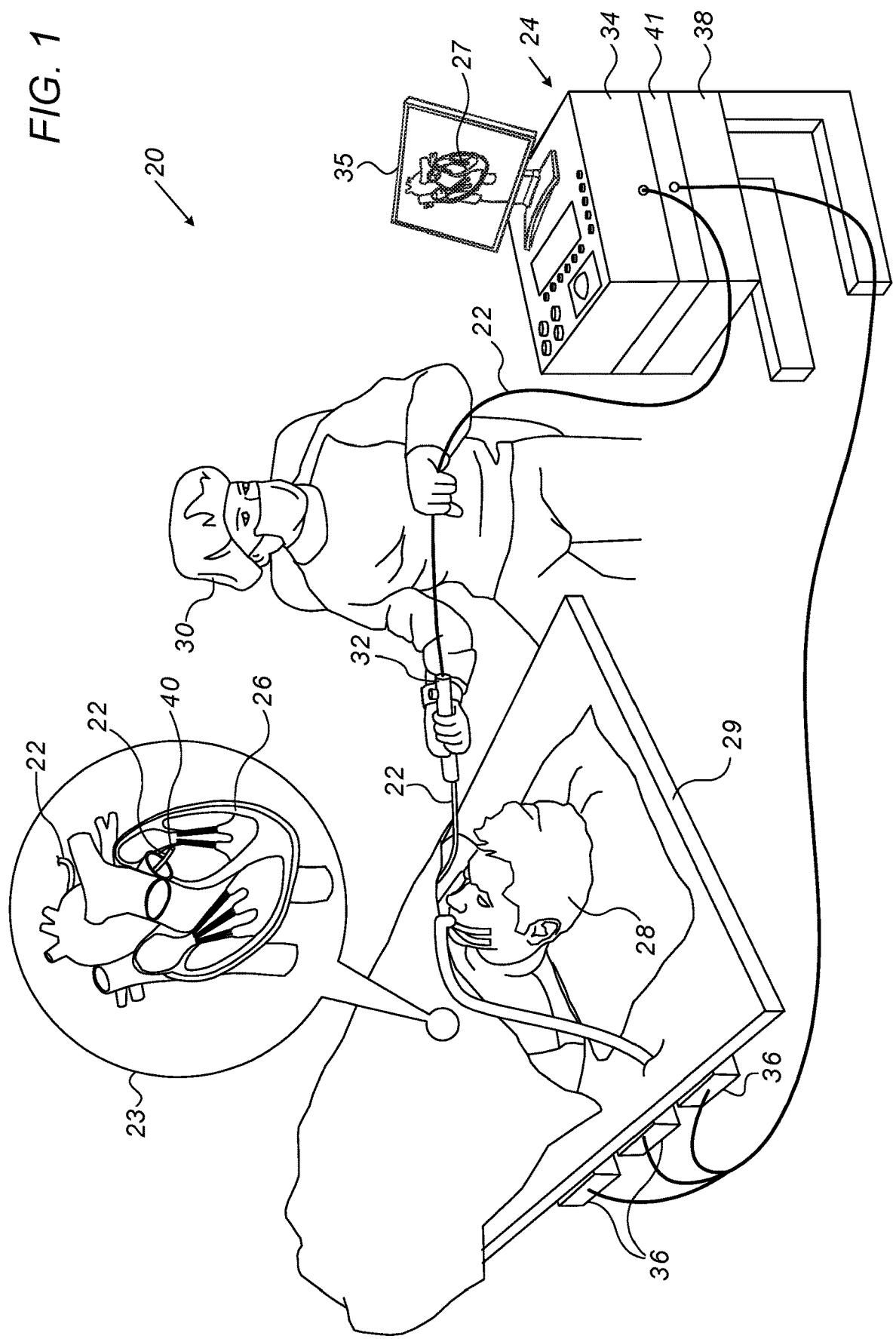
FIG. 1 is a schematic, pictorial illustration of a catheter-based tracking and ablation system, in accordance with an exemplary embodiment of the present invention.

During a minimally-invasive medical procedure, such as a cardiac ablation, a physician may use an anatomical map of the patient's heart with a displayed parameter that may help the physician to perform the ablation.

Some procedures require displaying of more than one parameter over the anatomical map. In principle, a number of anatomical maps can be displayed and a different parameter can be displayed over each of the maps. This method, however, requires the physician to switch between the maps during the procedure, and as a result, errors can occur in performing the procedure. For example, an error can occur when the physician assumes a value of a particular parameters (among a group of parameters) in an inaccurate position of the heart.

Exemplary embodiments of the present invention that are described hereinbelow provide improved techniques for presenting multiple parameters overlaid on one anatomical map. Such a presentation provides the physician with an indication of the numerical values of all the required parameters in different areas over the area of the anatomical map.

In some exemplary embodiments, a cardiac ablation system comprises a processor, which is configured to receive multiple datasets corresponding to multiple respective properties of the heart. Each dataset comprises multiple data points, such as measurements acquired at multiple sections of the heart, which are associated with respective sections of the heart. Each section corresponds to a different area on the surface of the anatomical map of the heart.

In some exemplary embodiments, the processor is configured to produce a map comprising visual attributes indicative of the measurements and/or other parameters, overlaid on the anatomical map. The processor is further configured to display, on a display of the system, the visual attributes overlaid on the anatomical map.

In some exemplary embodiments, the datasets may comprise measurements and/or calculations of various cardiac parameters acquired at various sections of the heart. For example, the cardiac parameters may comprise local activation time (LAT), peak-to-peak voltage, cycle length (CL) in atrial fibrillation, and standard deviation (STD) of the cycle length.

In some exemplary embodiments, the datasets may comprise output of one or more algorithms that enable detection of complex fractionated atrial electrograms (CFAEs) in an intra-cardiac electrocardiogram (IC-ECG), based on parameters defined by a user of the system (e.g., the physician). For example, (i) a shortest complex interval (SCI) for calculating a value of the shortest interval between two consecutive CFAEs in the IC-ECG signal, and (ii) if the IC-ECG signal comprises two or more adjacent CFAE complexes, an interval confidence level (ICL) provides the number of CFAE intervals. Additionally or alternatively, in ripples frequency of atrial fibrillation measured in voltage (mV) over time (ms), the datasets may comprise: (i) the number of detected peaks, and (ii) the percentage of signals having voltage higher than a predefined threshold.

In some exemplary embodiments, the processor is configured to produce a map comprising the anatomical map and two or more visual attributes of the respective parameters, which are overlaid on the anatomical map. The processor is further configured to display the map on the display of the cardiac ablation system. For example, the physician may select a pair of the parameters described above (e.g., LAT and peak-to-peak voltage, or the CL and the STD of the CL, or the SCI and ICL), the processor assigns a visual attribute to each of the selected parameters, and displays the visual attributes over the anatomical map of the heart.

In some exemplary embodiments, the processor is configured to replace or remove at least one of the parameters from the display, and to select any suitable combination of parameters to be displayed over an anatomical map of the heart, or on any other type of map of any other organ in question.

The disclosed techniques provide the physician with the capability to present any selected set of parameters overlaid on the anatomical map, and therefore, help to (i) improve the quality and (ii) shorten the cycle time, of the cardiac ablation procedures or any other medical procedure that requires displaying multiple parameters over a map of the organ in question.

System Description

FIG. 1 is a schematic, pictorial illustration of a catheter-based tracking and ablation system 20, in accordance with an exemplary embodiment of the present invention.

In some embodiments, system 20 comprises a catheter 22, in the present example a cardiac catheter, and a control console 24. In the exemplary embodiment described herein, catheter 22 may be used for any suitable therapeutic and/or diagnostic purposes, such as ablation of tissue in a heart 26.

In some exemplary embodiments, console 24 comprises a processor 41, typically a general-purpose computer, with suitable front end and interface circuits 38 for receiving signals via catheter 22 and for controlling the other components of system 20 described herein. Console 24 further comprises a user display 35, which is configured to receive from processor 41 a map 27 of heart 26, and to display map 27.

In some exemplary embodiments, map 27 may comprise any suitable type of anatomical map produced using any suitable technique. For example, the anatomical map may be produced using an anatomical image produced by using a suitable medical imaging system, or using a fast anatomical mapping (FAM) techniques using the CARTO™ system, produced by Biosense Webster Inc. (Irvine, Calif.), or using any other suitable technique, or using any suitable combination of the above.

In some exemplary embodiments, processor 41 is configured to receive multiple datasets corresponding to multiple respective properties of heart 26. Each dataset comprises multiple data points, such as measurements acquired at multiple sections of heart 26 or other sorts of parameters, which are associated with respective sections of heart 26. Each section corresponds to a different area on the surface of map 27.

In some exemplary embodiments, processor 41 is configured to produce map 27 comprising visual attributes (VAs) indicative of the measurements and/or other parameters, overlaid on map 27. Processor 41 is further configured to display, e.g., on display 35, the VAs overlaid on map 27, as will be shown and depicted in detail in FIG. 2 below.

In some exemplary embodiments, such as ablation of the heart tissue, a physician 30 may use map 27 having the VAs overlaid thereon, for planning the procedure in advance and/or during the ablation procedure.

Reference is now made to an inset 23. In some exemplary embodiments, when performing the ablation procedure, physician 30 inserts catheter 22 through the vasculature system of a patient 28 lying on a table 29. Catheter 22 comprises one or more ablation electrodes 40 fitted at its distal end. Electrodes 40 are configured to ablate tissue at a target location of heart 26. Physician 30 navigates the distal end in close proximity to the target location in heart 26 by using a manipulator 32 for manipulating catheter 22.

In other exemplary embodiments, catheter 22 may comprise sensing electrodes (not shown) configured to produce, in response to sensing electrophysiological (EP) signals in tissue of heart 26, signals indicative of the sensed EP signals. In such embodiments, the proximal end of catheter 22 is connected, inter alia, to interface circuits 38, so as to transfer these signals to processor 41.

In some exemplary embodiments, the position of the distal end in the heart cavity is measured using a position sensor (not shown) of a magnetic position tracking system. In the present example, console 24 comprises a driver circuit 34, which is configured to drive magnetic field generators 36 placed at known positions external to patient 28 lying on table 29, e.g., below the patient's torso. The position sensor is coupled to the distal end, and is configured to generate position signals in response to sensed external magnetic fields from field generators 36. The position signals are indicative of the position the distal end of catheter 22 in the coordinate system of the position sensing system.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

In some exemplary embodiments, the coordinate system of the position tracking system are registered with the coordinate systems of system 20 and map 27, so that processor 41 is configured to display on map 27, the position of the distal end of catheter 22.

In some exemplary embodiments, processor 41, typically comprises a general-purpose computer, which is programmed in software to carry out the functions described herein.

The software may be downloaded to the computer in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by exemplary embodiments of the present invention and to demonstrate the application of these embodiments in enhancing the performance of such a system. Exemplary embodiments of the present invention, however, are by no means limited to this specific sort of example system, and the principles described herein may similarly be applied to other sorts of medical systems.

Virtual Attributes Overlaid on Anatomical Map

Figure 2:
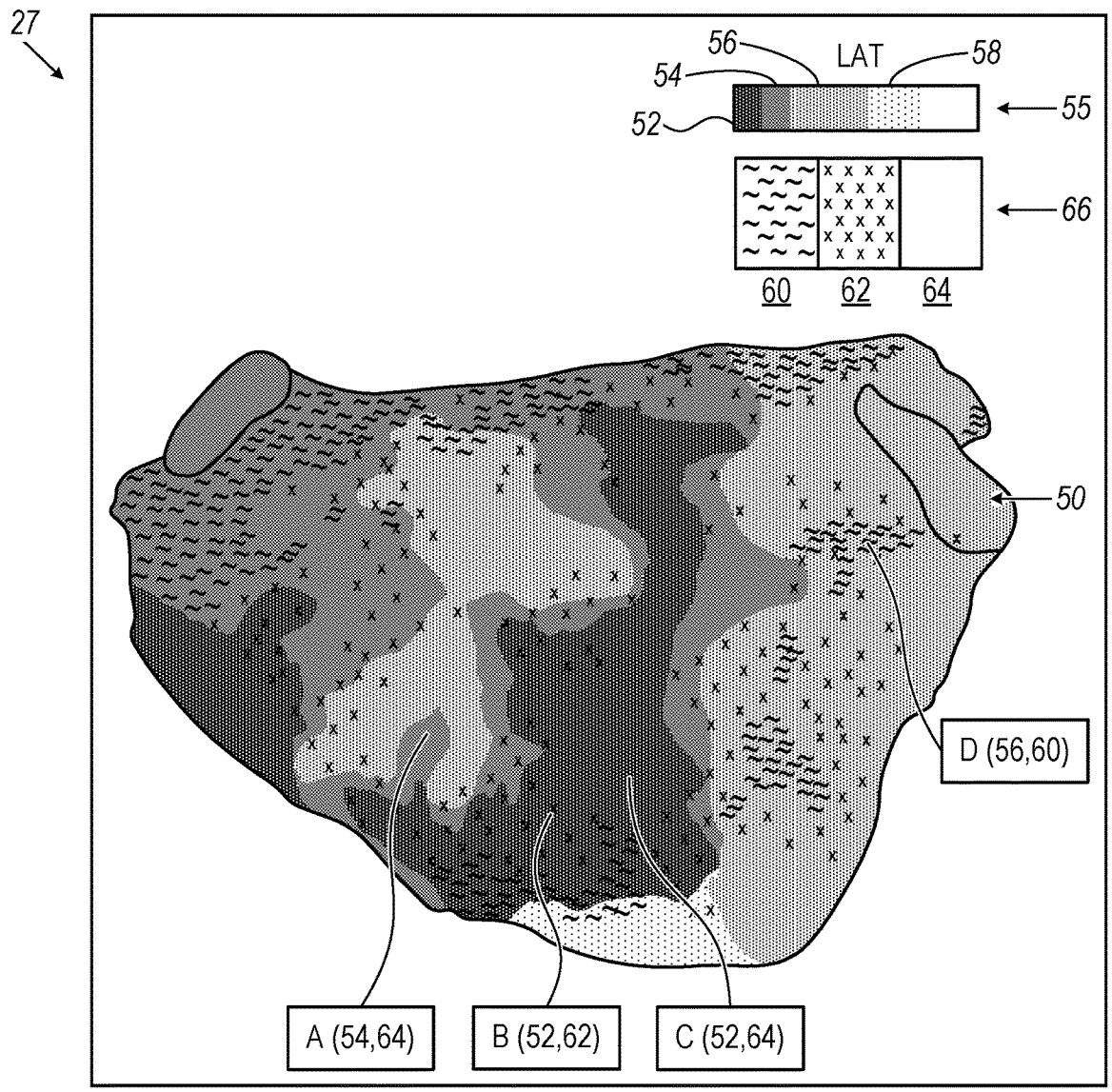
FIG. 2 is a schematic, pictorial illustration of multiple virtual attributes, which are indicative of respective parameters, and are overlaid on a map of patient heart, in accordance with an exemplary embodiment of the present invention.

FIG. 2 is a schematic, pictorial illustration of multiple virtual attributes, which are indicative of respective parameters, and are overlaid on map 27 of heart 26, in accordance with an exemplary embodiment of the present invention.

In some exemplary embodiments, processor 41 receives two datasets corresponding to two parameters measured at different sections of heart 26. In the present example, the first parameter corresponds to local activation times (LATs), and the second parameter corresponds to voltages. In the context of the present disclosure and in the claims, the term voltage may refer to peak-to-peak voltage measured in tissue of heart 26, or to any other voltage measured in any tissue of heart 26 or in tissue of any other organ of patient 28.

In some exemplary embodiments, processor 41 is configured to assign: (i) a first visual attribute (VA) 55 to the LAT measurements, and (ii) a second VA 66 to the voltage measurements.

In the present example, VA 55 comprises a color group arranged in a color scale having multiple colors and color gradients, each color indicative of a corresponding range of LATs relative to a predefined reference LAT. For example, a color 52 (e.g., red gradient) indicative of LATs between about −50 ms and −10 ms, a color 54 (e.g., yellow gradient) indicative of LATs between about 10 ms and 50 ms, a color 56 (e.g., green gradient) indicative of LATs between about 50 ms and 90 ms, and a color 58 (e.g., blue gradient) indicative of LATs between about 90 ms and 130 ms. Note that the negative values of LAT (e.g., between about −50 ms and −10 ms of the red gradient) are measured relative to the aforementioned predefined reference LAT.

In some exemplary embodiments, VA 66 comprises a texture scale having multiple types of textures, each texture is indicative of a corresponding range of voltages. In the present example, VA 66 comprises: (i) a texture 60 having a wavy shape and indicative of low voltages (e.g., between about 0.05 mV and 0.5 mV), (ii) a texture 62 having an array of "X" shapes and indicative of medium voltages (e.g., between about 0.5 mV and 1.5 mV), and (iii) a texture 64, which is blank (i.e., without any pattern) and is indicative of high voltages (e.g., about 1.5 mm mV). Grey scale, shading and/or shading are utilized to represent color in this application.

In the context of the present disclosure and in the claims, the terms "about" or "approximately" for any numerical values or ranges indicate a suitable dimensional tolerance that allows the part or collection of components to function for its intended purpose as described herein.

In some exemplary embodiments, based on the datasets and assigned VAs 55 and 66, processor 41 is configured to produce map 27 comprising an overlay of VAs 55 and 66 for each section of map 27, and to display the map on display 35. For example: (i) a section "A" has a color 54 and a texture 64, (ii) a section "B" has a color 52 and a texture 62), (iii) section "C" has a color 52 and a texture 64, and (iv) section "D" positioned in close proximity to an ostium 50 of heart 26, has a color 56 and a texture 60.

In some exemplary embodiments, map 27 with the overlaid LAT and voltage provides physician 30 with a presentation indicative of two or more parameters at each section of heart 26. For example, sections "B" and "C" are in close proximity and have similar LAT but different voltage, and section "D" that has low voltage is surrounded with sections having medium and mainly high voltage.

In principle, it is possible to produce multiple maps, each of which having one parameter overlaid on the map of heart 26, however, such presentation cannot provide physician with the presented combination of two or more parameters at sections of interest of heart 26.

In other exemplary embodiments, processor 41 is configured to produce map 27 with more than two parameters, for example, using different sets of patterns and/or numbers and/or any other suitable notifications for each type of parameter.

In alternative exemplary embodiments, instead of or in addition to LAT and voltage, processor 41 is configured to produce map 27 having other visual attributes indicative of other parameters, such as but not limited to cycle length in atrial fibrillation and standard deviation of the aforementioned cycle length.

In some exemplary embodiments, the datasets may comprise output of one or more algorithms that enable detection of complex fractionated atrial electrograms (CFAEs) in an intra-cardiac electrocardiogram (IC-ECG), based on parameters defined by physician 30. For example, (i) a shortest complex interval (SCI) for calculating a value of the shortest interval between two consecutive CFAEs in the IC-ECG signal, and (ii) if the IC-ECG signal comprises two or more adjacent CFAE complexes, an interval confidence level (ICL) provides the number of CFAE intervals. Additionally or alternatively, in ripples frequency of atrial fibrillation measured in voltage (mV) over time (ms), the datasets may comprise: (i) the number of detected peaks, and (ii) the percentage of signals having voltage higher than a predefined threshold.

This particular set of visual attributes, e.g., colors and the textures shown in FIG. 2 and/or described above, is provided by way of example, in order to illustrate certain problems that are addressed by embodiments of the present invention and to demonstrate the application of these embodiments in enhancing the performance of such a system. Embodiments of the present invention, however, are by no means limited to these specific sort of example parameters and/or visual attributes, and the principles described herein may similarly be applied to other sorts of maps having any other suitable parameters and/or visual attributes.

Figure 3:
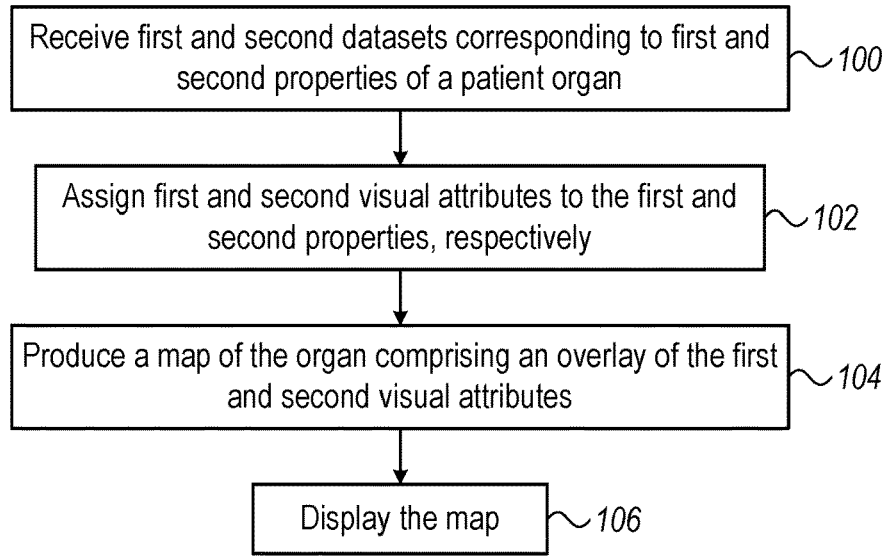
FIG. 3 is a flow chart that schematically illustrates a method for presenting multiple parameters overlaid on a heart map, in accordance with an exemplary embodiment of the present invention.

FIG. 3 is a flow chart that schematically illustrates a method for presenting multiple parameters overlaid on map 27, in accordance with an exemplary embodiment of the present invention.

The method begins at a datasets receiving step 100, with processor 41 (or any other suitable device) configured to receive first and second datasets corresponding to first and second properties of heart 26 or any other organ of patient 28, in the present example the parameters may comprise measurements acquired in heart 26, as described in detail in FIGS. 1 and 2 above.

At a visual attribute assignment step 102, processor 41 (or any other suitable device) assigns first and second visual attributes, such as VAs 55 and 66 described in detail in FIG. 2 above, to the first and second properties (e.g., LAT and voltage), respectively.

At a map producing step 104, processor 41 (or any other suitable device) produces map 27 of heart 26 or any other organ as described above. In some exemplary embodiments, map 27 comprises an anatomical map of heart 26 (obtained using any suitable technique) with VAs 55 and 66 overlaid on the anatomical map.

At a map displaying step 106 that concludes the method, processor 41 (or any other suitable device) displays map 27 on any suitable output device, such as but not limited to, display 35 as described in detail in FIG. 2 above.

Although the exemplary embodiments described herein mainly address presentation of atrial fibrillation (AF) parameters on a cardiac anatomical map, the methods and systems described herein can also be used in other parameters of AF, such as in displaying regular cycle length (CL) during AF with standard deviation (STD) of the CL, wherein the section with minimal value of CL and STD of CL is intended to be ablated. Moreover, the methods and systems described herein can also be used in other applications, such as in presenting over an anatomical map multiple parameters of ventricle fibrillation, or any other two or more parameters presented over any anatomical map of any organ in question.

It will thus be appreciated that the exemplary embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for visualizing multiple parameters overlaid on an electroanatomical map, the system comprising:
   a processor, which is configured to: (i) receive a first dataset corresponding to a first property of an organ of a patient, and a second dataset corresponding to a second property of the organ, (ii) assign a first visual attribute to the first property and a second visual attribute to the second property, and (iii) produce a map of the organ comprising an overlay of the first and second visual attributes, wherein the organ comprises a heart, and wherein the first and second properties are selected from a list of electrophysiological properties consisting of: a voltage, a local activation time (LAT), a cycle length (CL) of an atrial fibrillation, and a standard deviation (STD) of the CL; and
   a display, which is configured to display the map.

2. The system according to claim 1, wherein the first dataset comprises first measurements of the first property and the second dataset comprises second measurements of the second property, wherein the first visual attribute comprises a color group comprising multiple colors, and the second visual attribute comprises a texture group comprising multiple texture types, and wherein the processor is configured to map the first measurements into respective colors of the color group, and the second measurements into respective textures of the texture group.

3. The system according to claim 2, wherein the map comprises multiple sections on a surface of the organ, wherein each of the multiple sections comprises at least one of the first and second measurements, and wherein the processor is configured, at each of the multiple sections, to: (a) check for the first and second measurements, and (b) assign to the map at least one of: (i) a color of the respective colors, which are corresponding to the first measurements, and (ii) a texture of the textures, which are corresponding to the second measurements.

4. A method for visualizing multiple parameters overlaid on an electroanatomical map, the method comprising:
   receiving a first dataset corresponding to a first property of an organ of a patient, and a second dataset corresponding to a second property of the organ;
   assigning a first visual attribute to the first property and a second visual attribute to the second property;
   producing a map of the organ comprising an overlay of the first and second visual attributes, wherein the organ comprises a heart, and wherein the first and second properties are selected from a list of electrophysiological properties consisting of: a voltage, a local activation time (LAT), a cycle length (CL) of an atrial fibrillation, and a standard deviation (STD) of the CL; and displaying the map.

5. The method according to claim 4, wherein receiving the first dataset comprises receiving first measurements of the first property and receiving the second dataset comprises receiving second measurements of the second property, wherein (i) assigning the first visual attribute comprises assigning a color group comprising multiple colors, and mapping the first measurements into respective colors of the color group, and (ii) assigning the second visual attribute comprises assigning a texture group comprising multiple texture types, and mapping the second measurements into respective textures of the texture group.

6. The method according to claim 5, wherein the map comprises multiple sections on a surface of the organ, wherein each of the multiple sections comprises at least one of the first and second measurements, and wherein assigning the first and second visual attributes comprises, at each of the multiple sections, to: (a) checking for the first and second measurements, and (b) assigning to the map at least one of: (i) a color of the respective colors, which are corresponding to the first measurements, and (ii) a texture of the textures, which are corresponding to the second measurements.

* * * * *